United States Patent
Goto

(10) Patent No.: US 7,044,781 B2
(45) Date of Patent: May 16, 2006

(54) HYBRID SEALED HOUSING HEADER

(75) Inventor: Kazuhiro Goto, Markham (CA)

(73) Assignee: Tyco Electronics Canada, Ltd., Ontario (CA)

(*) Notice: Subject to any disclaimer, the term of this patent is extended or adjusted under 35 U.S.C. 154(b) by 152 days.

(21) Appl. No.: 10/865,316

(22) Filed: Jun. 10, 2004

(65) Prior Publication Data

US 2004/0253868 A1  Dec. 16, 2004

Related U.S. Application Data

(60) Provisional application No. 60/479,633, filed on Jun. 19, 2003.

(51) Int. Cl.
*H01R 13/73* (2006.01)

(52) U.S. Cl. .................................. 439/559; 439/926
(58) Field of Classification Search ............. 439/559, 439/558, 556, 544, 548, 926, 949, 76.1
See application file for complete search history.

(56) References Cited

U.S. PATENT DOCUMENTS 2,915,734 A * 12/1959 Alden ..................... 439/608
4,555,638 A * 11/1985 Lobe ....................... 307/10.1

* cited by examiner

*Primary Examiner*—Phuong Dinh

(57) ABSTRACT

The invention provides a header for receiving a mating plug. The header is mountable to a sealed housing. A bottom wall of the header features a flange receiving opening for allowing a portion of the bottom wall to pass into a flange of the sealed housing. A plurality of contact receiving passageways passing through the bottom wall are positioned between portions of the flange receiving opening. At least one external contact receiving passageway passes through the bottom wall in the position which is adjacent to and outside of at least a portion of the flange receiving opening. This header allows electrical signals to be carried through the bottom wall both into the sealed assembly and also to other locations outside of the sealed assembly.

12 Claims, 3 Drawing Sheets

HYBRID SEALED HOUSING HEADER

RELATED APPLICATIONS

This application claims the benefit of U.S. Provisional Application No. 60/479,633 filed Jun. 19, 2003.

FIELD OF THE INVENTION

The invention is related to electrical connectors and more particularly to a header for a lamp housing.

BACKGROUND OF THE INVENTION

Automotive electrical distribution systems usually include a main vehicle wiring harness which is manufactured as a sub-assembly. The main vehicle wiring harness includes a plurality of electrical connectors for receiving electrical signals and for outputting those electrical signals to various components of the vehicle such as engine control systems, lighting systems, climate control systems, audio systems, and all other vehicle systems. On an assembly line, the main wiring harness is placed within the vehicle and the plurality of electrical connectors are mated with various signal sources and component systems. These connectors are usually sealed, keyed and often times include terminal position assurance and connector position assurance features.

In one known application, a main vehicle wiring harness includes a lighting plug which is designed to output power to the vehicle's external lamps. For example, the lighting plug includes output for the headlights, tail lights, turn signals, and parking lights. These outputs must be efficiently distributed from the lighting plug to the appropriate vehicle lamps. One known distribution method is shown in the prior art of FIG. 1 wherein the lamp plug (not shown) is mated with a header 2 mounted within an opening 3 of a sealed headlamp housing 4. This arrangement requires the header 2 to remain sealed in order to preserve the integrity of the sealed head lamp housing 4. Since the lamp plug contains output wires for controlling power to both the sealed headlamp 4 and the remaining tail lamps, turn signals 5, and parking lamps 6, it is necessary to also distribute those output wires from the lamp plug to their respective lamp destinations. In the prior art, this is accomplished by connecting wires from the lamp side of the header 2 through the sealed head lamp housing 4 to another sealed output connector 7 which is sealed within a second opening 8 of the sealed head lamp housing 4. The sealed output connector 7 mates with another plug (not shown) for carrying wire, controlling power to the other lamps such as turn signals 5 and parking lamps 6. This arrangement presents a problem in that two openings 3, 8 are required in the sealed lamp housing 4 thus creating a greater risk of compromising the seal. Also, two connectors 2, 7 and two sets of sealing hardware are required. It is desirable to reduce the risk of compromising the seal in the head lamp housing or within other sealed housings and also to reduce the number of connectors required for distribution of these lamp output signals.

SUMMARY OF THE INVENTION

The invention provides a header for receiving a mating plug. The header is mountable to a sealed housing. A bottom wall of the header features a flange receiving opening for allowing a portion of the bottom wall to pass into a flange of the sealed housing. A plurality of contact receiving passageways passing through the bottom wall are positioned between portions of the flange receiving opening. At least one external contact receiving passageway passes through the bottom wall in a position which is adjacent to and outside of at least a portion of the flange receiving opening. This header allows electrical signals to be carried through the bottom wall both into the sealed assembly and also to other locations outside of the sealed assembly. Furthermore, it is desirable to provide a single point of termination for connector to the main vehicle wiring harness.

BRIEF DESCRIPTION OF THE DRAWINGS

The invention will now be described by way of example with reference to the accompanying figures of which.

DETAILED DESCRIPTION OF THE INVENTION

Figure 2:
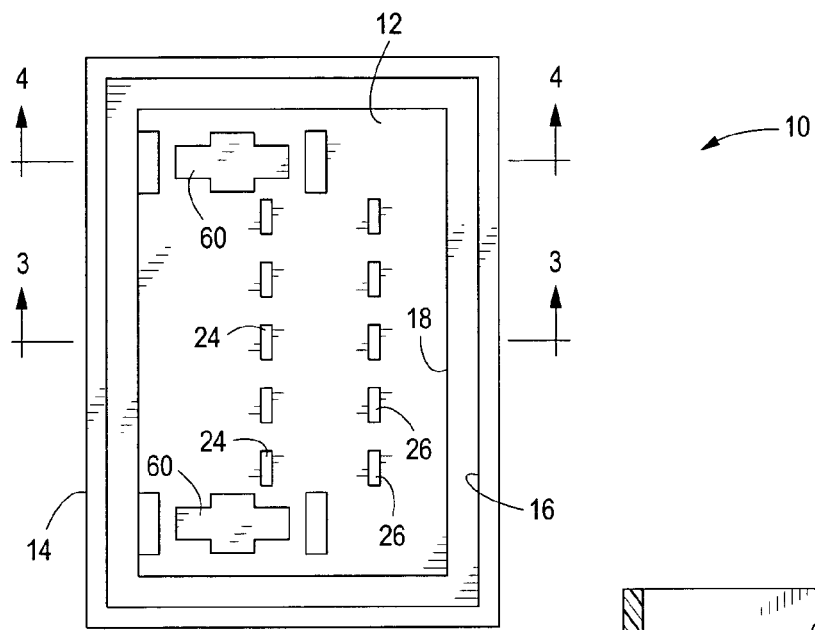
FIG. 2 is a top view of a header according to the present invention.

The invention will first be described generally with reference to FIGS. 2 and 3. A header 10 is shown having a plug receiving section 12 bounded by a peripheral wall 14. The peripheral wall 14 consists of a sealing portion 16 which extends upward from a plug engaging portion 18. The plug engaging portion 18 is relatively narrower than the sealing portion 16 and is connected to the sealing portion 16 by a ledge 20 which extends generally perpendicular to the sealing portion 16 and the plug engaging portion 18. The plug engaging portion 18 is located near a bottom wall 22 which is also bounded by the peripheral wall 14. The plug engaging portion 18 extends upward from the bottom wall 22 and the sealing portion 16 extends upward from the ledge 20 which is connected to the plug engaging portion 18. The bottom wall 22 features a plurality of first internal contact receiving passageways 24 passing therethrough and a plurality of external contact receiving passageways 26 also passing therethrough. The internal contact receiving passageways 24 are arranged in a first row while the external contact receiving passageways 26 are arranged in a second row. Internal contacts 28 are secured in the internal contact receiving passageways 24 while external contacts 30 are secured in the external contact receiving passageways 26. It should be understood that while the internal and external contacts 28, 30 are shown as being pin contacts, other male or female contacts which terminate a wire are within the scope of the invention. The internal contacts 28 terminate internal wires 34 which enter the sealed housing 50 while the external contacts 30 terminate external wires 36 which go to other lamps or components outside the sealed housing 50.

Figure 4:
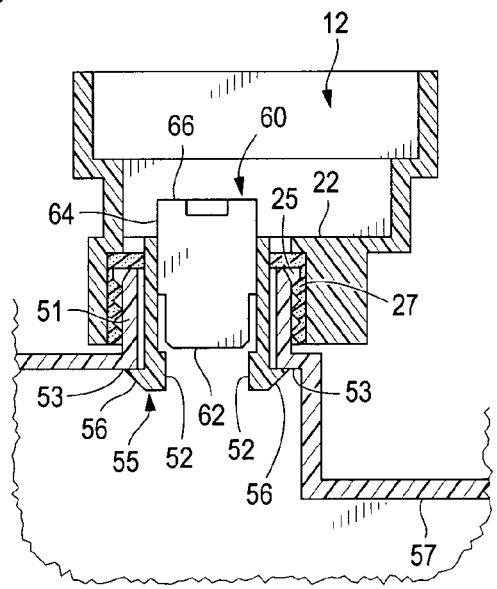
FIG. 4 is a cross sectional view of the header of FIG. 2 taken along the line 4—4 being mounted to a sealed housing.
Figure 5:
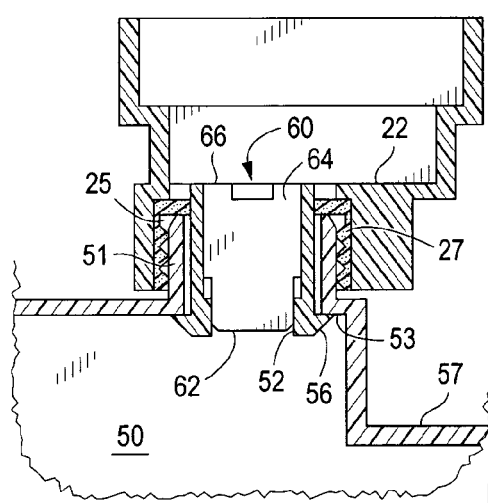
FIG. 5 is a cross sectional view similar to that of FIG. 4 wherein the secondary latch is engaged.

A pair of primary latches 55 extend outward from the bottom wall 22. Each primary latch 55 consists of a pair of cantilever arms 54 being attached to the bottom wall 22 and extending outward therefrom to a free end. A catch 56 is located at the free end of each cantilever arm 54. A back surface 52 is provided adjacent to and generally behind each catch 56. Positioned within the bottom wall 22 adjacent to the two rows of contact receiving passageways 24, 26 are a plurality of movable secondary latches 60. As best shown in FIGS. 4 and 5, the secondary latch 60 is profiled to have a narrow portion 62 towards its bottom surface and a wide portion 64 extending upward from the narrow portion to a top surface 66. Although the secondary latches 60 are shown as having a "T" shaped configuration in FIG. 2, other geometries are achievable which have the narrow to wide profile described above. A flange receiving opening 25 is formed in the bottom wall 22 and is open to the underside or outside of the header 10. A header seal 27 is positioned within the flange receiving opening 25. A plurality of internal contacts 28 are positioned and secured within the internal contact receiving passageways 24. Likewise, a plurality of external contacts 30 are positioned within external contact receiving passageways 26. A wire seal 32 is positioned around each external wire and sealingly engaged within the external contact receiving passage way 26.

Figure 3:
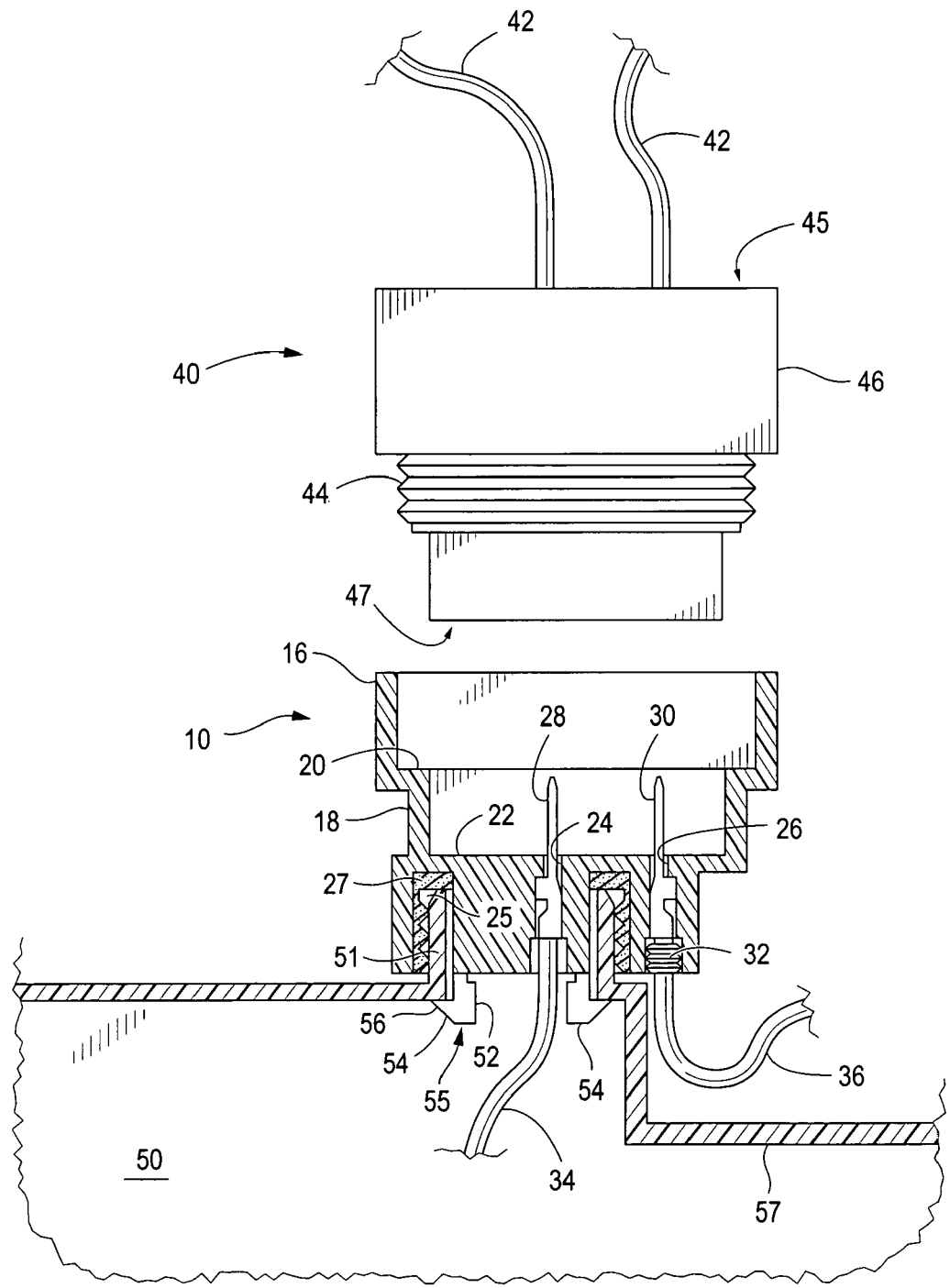
FIG. 3 is a cross sectional view of the header of FIG. 2 taken along the line 3—3 showing a plug positioned for mating with the header.

As best shown in FIG. 3, a plug 40 is matable with the header 10 and has a plurality of harness wires 42 entering a housing 46. Typical terminations are provided within the housing 46 and in this case, would include a plurality of female contacts being crimped onto stripped ends of the harness wires 42. The housing 46 is profiled to have a mating end 47 which is narrower than a wire receiving end 45. A plug seal 44 is provided around the mating end 47. When mated with the header 10, the mating end 47 is received within the plug engaging portion 18 of the peripheral wall 14 while the plug seal 44 is received against the sealing portion 16 of the peripheral wall 14.

Figure 1:
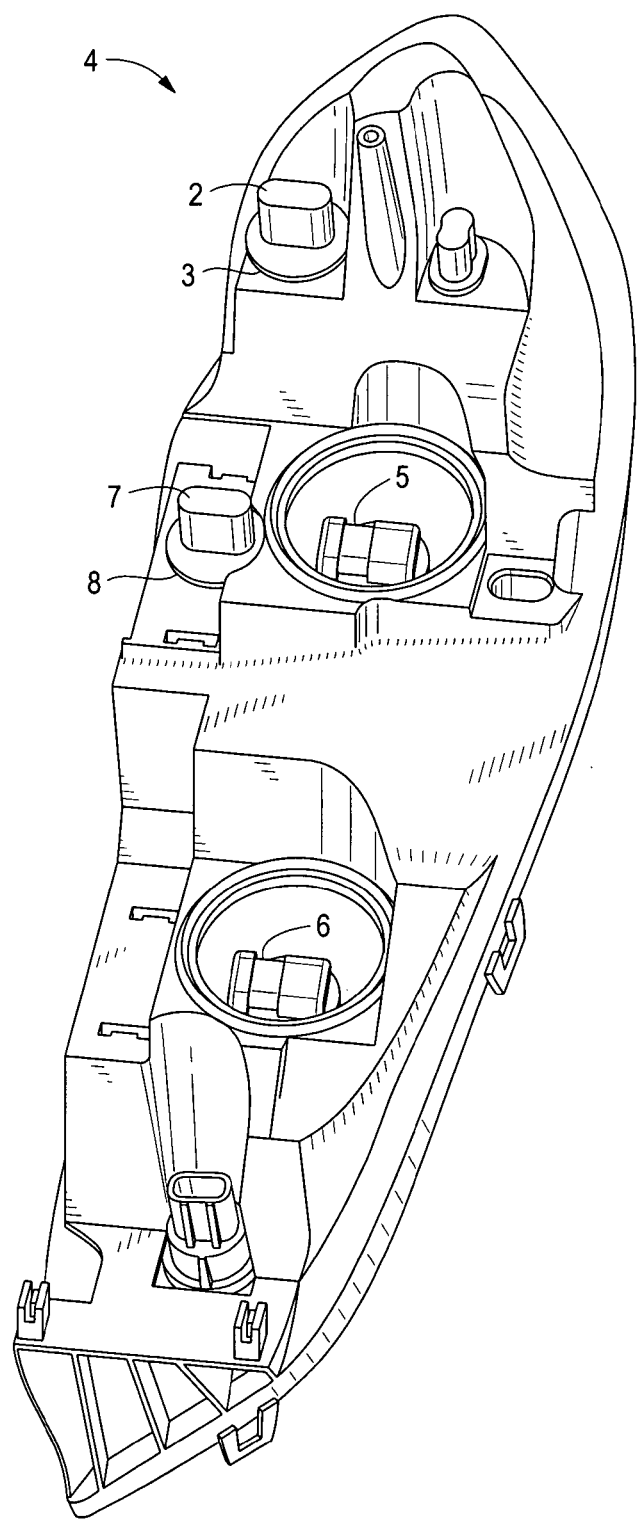
FIG. 1 is a perspective view of a prior art sealed head lamp arrangement having a sealed input electrical connector and a sealed output electrical connector.

Securing of the header 10 to a sealed housing 50, such as a head lamp housing, will now be described in greater detail with reference to FIGS. 4 and 5. It should be understood that the figures show only an enlarged portion of the sealed housing 50 which has an opening defined by a housing flange 51 extending outwardly from the opening. Those skilled in the art will appreciate that the broken lines shown in the drawings indicate housing walls 57 that meet with each other in another location to form a closed housing, such as a sealed head lamp housing 4, as shown in FIG. 1. A locking surface 53 is formed in the housing wall 57 and is located under the housing flange 51. The header 10 is positioned over the opening such that the housing flange 51 is received within the flange receiving opening 25. The header seal 27 engages the housing flange 51 to provide a seal between the header 10 and the housing flange 51. The header 10 is urged into the opening such that the catches 56 and cantilever arms 54 initially resile inward and then snap outward to engage and lock behind the locking surface 53. The secondary latch 60 is then urged between the cantilever arms 54 such that the narrow portion 62 engages the back surfaces 52 to ensure that the catches 56 are fully urged outward and locked against the locking surfaces 53. If the cantilever arms 54 are not fully inserted such that the catches 56 are locked on the locking surfaces, the secondary latch 60 will not be fully insertable and will remain in the position shown in FIG. 4 to block the insertion of a plug 40 into the plug receiving section 12. Upon full insertion of the secondary latch 60 as show in FIG. 5, the cantilever arms 54 will be appropriately positioned such that the catches 56 are locked on the locking surface 53 and the top surface 66 of the secondary latch 60 is flush with the top surface of the bottom wall 22 to allow entry of the plug 40 into the plug receiving section 12. Although a preferred embodiment comprises primary and secondary latches as described above, one skilled in the art would be aware of alternative latching configurations that would be suitable.

Once the plug 40 is mated with the header 10, as can be best seen in FIG. 3, the header 10 is capable of distributing signals within the sealed housing 50 through internal contacts 28 and also capable of distributing signals to other components external to the sealed housing 50 through external contacts 30 within the same header 10. This is advantageous because it provides a single point of termination and thus eliminates the need for a second connector to be positioned within a second opening of the sealed housing 50 in order to distribute signals to external components. This arrangement also eliminates the added possibility of compromising the seal within the sealed housing by creating another opening therein.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A header for receiving a mating plug comprising:
   a bottom wall having a flange receiving opening for allowing a portion of the bottom wall to pass into a flange of a sealed housing;
   a plurality of internal contact receiving passageways passing through the bottom wall and positioned to be between portions of the flange receiving opening; and,
   at least one external contact receiving passageway passing through the bottom wall in a position adjacent to and outside of at least a portion of the flange receiving opening;
   whereby electrical signals are carried through the bottom wall both into the sealed housing and to other locations outside of the sealed housing simultaneously.

2. The header of claim 1 further comprising a header seal being positioned within the flange receiving opening for sealingly receiving the flange of the sealed housing.

3. The header of claim 1 further comprising at least one primary latch extending outward from the bottom wall.

4. The header of claim 3 wherein the primary latch includes a pair of cantilever arms each being fixed to the bottom wall and extending to a free end having a catch.

5. The header of claim 4 wherein the cantilever arms each further include a back surface positioned adjacent to and generally behind the catch.

6. The header of claim 5 wherein the catch engages a locking surface of the sealed housing when fully seated.

7. The header of claim 6 further comprising a secondary latch being profiled to have a narrow portion at a bottom end and a wide portion at a top end.

8. The header of claim 7 wherein the secondary latch is insertable adjacent to the pair of cantilever arms of the primary latch.

9. The header of claim 8 wherein the narrow portion of the secondary latch engages the back surface of cantilever arm when properly seated.

10. The header of claim 1 further comprising a plurality of internal contacts being secured within the plurality of internal contact receiving passageways, the internal contacts being terminated to internal wires which enter the sealed housing.

11. The header of claim 1 wherein at least one external contact is secured within the external contact receiving passageway and is terminated to an external wire which passes outside of the sealed housing.

12. The header of claim 11 further comprising a seal being located around the external wire and within the external contact receiving passageway.

* * * * *